(12) United States Patent
Havel et al.

(10) Patent No.: US 8,140,171 B2
(45) Date of Patent: Mar. 20, 2012

(54) SUBCUTANEOUS IMPLANTABLE LEAD

(75) Inventors: William J. Havel, Maple Grove, MN (US); Markus J. C. Lazeroms, Vroenhoven-Riemst (BE); Jean J. G. Rutten, Bocholtz (NL); Karel F. A. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 603 days.

(21) Appl. No.: 12/183,568

(22) Filed: Jul. 31, 2008

(65) Prior Publication Data
US 2010/0030291 A1  Feb. 4, 2010

(51) Int. Cl.
*A61N 1/00* (2006.01)

(52) U.S. Cl. ............. 607/116; 607/5; 607/119; 607/122

(58) Field of Classification Search .............. 607/5, 116, 607/119, 122
See application file for complete search history.

(56) References Cited

U.S. PATENT DOCUMENTS

| | | |
|---|---|---|
| 4,913,164 A | 4/1990 | Greene et al. |
| 4,953,551 A | 9/1990 | Mehra et al. |
| 5,044,374 A | 9/1991 | Lindemans et al. |
| 6,093,172 A | 7/2000 | Funderburk et al. |
| 7,069,075 B2 | 6/2006 | Olson |
| 7,092,765 B2 | 8/2006 | Geske et al. |
| 7,236,828 B2 | 6/2007 | Casavant et al. |
| 7,286,884 B2 | 10/2007 | Marshall et al. |
| 7,383,085 B2 | 6/2008 | Olson |
| 2002/0107545 A1* | 8/2002 | Rissmann et al. ................ 607/5 |
| 2002/0151948 A1 | 10/2002 | King et al. |
| 2004/0230229 A1 | 11/2004 | Lovett et al. |
| 2006/0004421 A1 | 1/2006 | Bennett et al. |
| 2006/0020316 A1* | 1/2006 | Martinez et al. .............. 607/122 |
| 2007/0203556 A1 | 8/2007 | Rutten et al. |

FOREIGN PATENT DOCUMENTS

WO  20080106338 A  9/2008

* cited by examiner

*Primary Examiner* — Nicole F Lavert
(74) *Attorney, Agent, or Firm* — Michael C. Soldner

(57) ABSTRACT

A subcutaneous implantable device is provided that includes a defibrillation electrode disposed along a portion of a lead, and a lead tip connected to the lead. The lead tip includes a trailing end coupled to a distal end of the lead, and first and second non-parallel sides extending from the trailing end that converge to a leading end that is configured to wedge between tissue layers as the lead is advanced subcutaneously.

14 Claims, 10 Drawing Sheets

SUBCUTANEOUS IMPLANTABLE LEAD

FIELD OF THE INVENTION

The present invention relates generally to subcutaneous implantable leads, and more particularly, to a subcutaneous implantable lead having a lead tip configured to assist in subcutaneously tunneling the lead without the use of a sheath.

BACKGROUND OF THE INVENTION

Many types of implantable medical devices have been clinically implanted into patient's bodies over the last twenty years that deliver relatively high-energy cardioversion and/or defibrillation shocks to a patient's heart when a malignant tachyarrhythmia, e.g., atrial or ventricular fibrillation, is detected. Cardioversion shocks are delivered in synchrony with a detected R-wave when fibrillation detection criteria are met, whereas defibrillation shocks are delivered when fibrillation criteria are met and an R-wave cannot be discerned from the electrocardiogram. The earliest clinically released automatic implantable defibrillators (AIDs) that were implanted in human patients provided a high energy defibrillation shock developed by an AID implantable pulse generator (IPG) through a pair of epicardial electrodes applied directly to the epicardium of the heart exposed through a thoracotomy when high heart rate detection criteria were met. Later developed and clinically implanted implantable cardiodefibrillators (ICDs), originally referred to as pacemaker/cardioverter/defibrillators (PCDs), possessed more sophisticated detection algorithms and provided defibrillation, R-wave synchronized cardioversion, and pacing therapies to treat a variety of malignant tachyarrhythmias ranging from fibrillation to fast tachycardias. Current ICDs typically additionally possess single or dual chamber bradycardia pacing capabilities for treating specified chronic or episodic atrial and/or ventricular bradycardia and tachycardia. The most current clinically released ICDs also include right and left heart chamber pacing capabilities for improving the cardiac output of patient's hearts that are in heart failure. Unless otherwise indicated, all of the above-described IMDs are referred to herein as ICDs.

It was postulated early in the development of ICDs that cardioversion/defibrillation shocks could be delivered between large surface area patch electrodes implanted subcutaneously over the ribcage on either side of the heart as indicated in the article by Schuder et al. entitled "Experimental Ventricular Defibrillation with an Automatic and Completely Implanted System", Transactions American Society for Artificial Internal Organs, 16:207, 1970.

Subcutaneous leads are implanted between the patient's skin and rib cage with a tunneling tool. Conventional subcutaneous implantable leads are implanted by first forming a subcutaneous channel with a tunneling tool that is coaxial with a sheath. After the channel is formed, the tool is removed leaving the sheath disposed in the channel. The lead is subsequently threaded down the sheath into a desired subcutaneous position. The sheath is thereafter removed by withdrawing and slitting the sheath to bring the sheath over a proximal end of the lead. Withdrawing the sheath from the channel can undesirably snag the lead and move it from is desired subcutaneous position.

It is desirable to provide implantable leads for use with ICDs that are simpler to place subcutaneously.

DETAILED DESCRIPTION OF THE INVENTION

According to an embodiment of the present invention, a subcutaneous implantable device is provided having an arrow-shaped lead tip configured to enable subcutaneous placement of the lead without introducing the lead down a sheath. The lead tip is configured to enable direct placement of the lead with a tunneling tool and minimizes the possibility of undesirably puncturing the thoracic muscle or skin.

In one embodiment, the arrow-shaped lead tip includes a trailing end that is coupled to the lead, and first and second non-parallel sides extending from the trailing end that converge to a leading end that is configured to wedge between tissue layers as the lead is advanced subcutaneously.

In one embodiment, the lead tip provides increased electrically conductive surface for the lead, which contributes to improved defibrillation shock delivery.

It is to be understood that features of the various exemplary embodiments described herein may be combined with each other, unless specifically noted otherwise.

Figure 1:
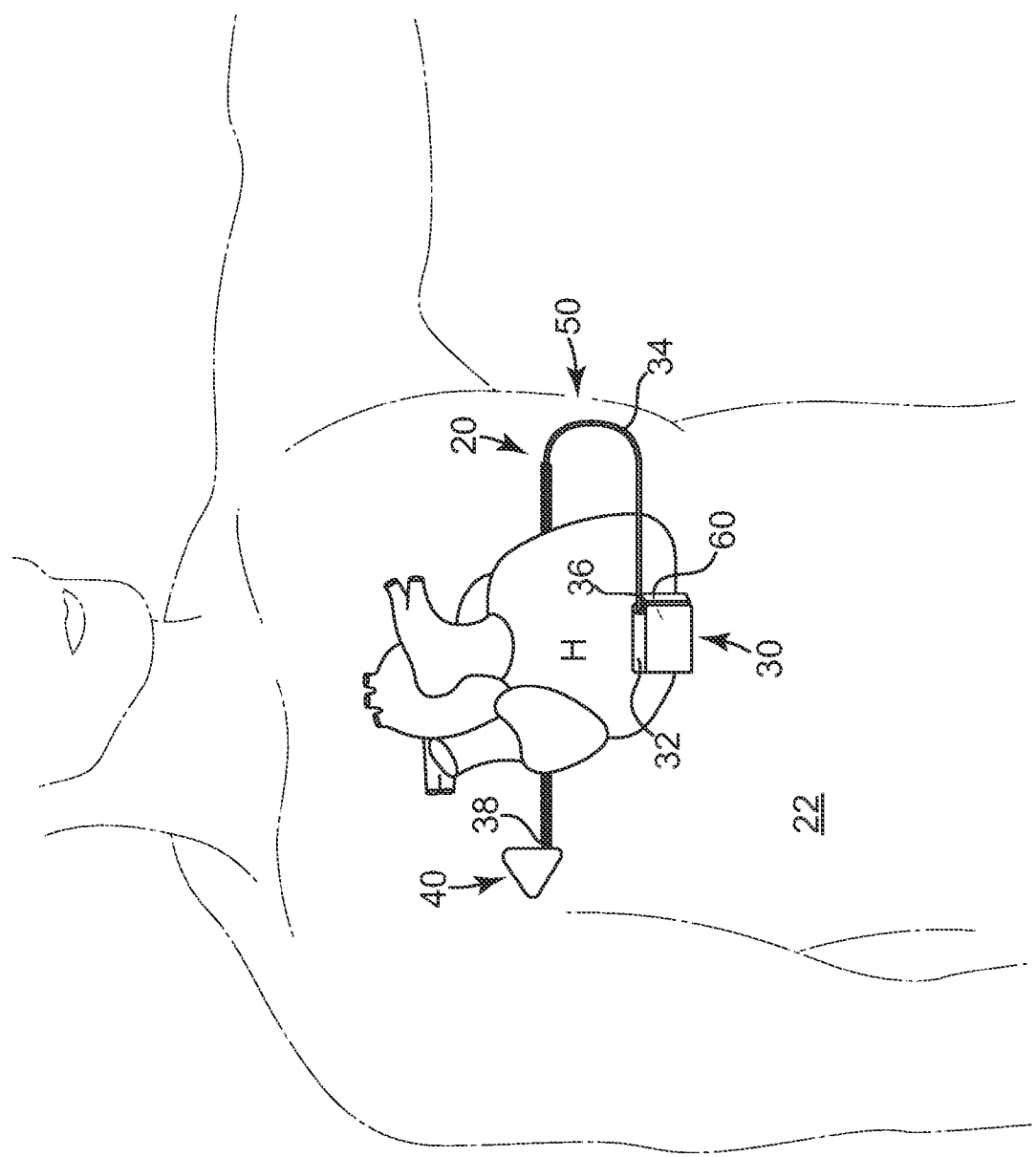
FIG. 1 is a schematic illustration of an implanted implantable cardiodefibrillator (ICD) including a subcutaneous implantable lead attached to a lead tip according to one embodiment.

FIG. 1 is a schematic illustration of an implantable cardiodefibrillator (ICD) 20 subcutaneously implanted in a patient 22 according to one embodiment. ICD 20 includes a housing 30 including a header 32, a lead 34 including a proximal end 36 coupled to header 32 and a distal end 38 coupled to a lead tip 40. In one embodiment, lead tip 40 is tunneled subcutaneously through an incision 50 to place lead 34 between the patient's 22 skin and rib cage in the region of the heart H. Thereafter, proximal end 36 of lead 34 is connected to header 32 and housing 30 is subcutaneously implanted pectorally within patient 22 between the skin and rib cage.

ICD 20 is implanted subcutaneously outside the thorax and inside the skin. Suitable implantation sites include a posterior region of the patient's rib cage, a paraspinal region of the patient, a parascapular region of the patient, or approximately posterior to a midaxillary line of the patient. In one embodiment, ICD 20 provides subcutaneous defibrillation and pacing without implanted venous epicardial leads. In one embodiment, ICD 20 provides subcutaneous defibrillation and pacing in addition to one or more implanted venous epicardial leads that connect to circuitry within housing 30.

In one embodiment, housing 30 is hermetically sealed to enclose electronic sensing, pacing, and cardioversion/defibrillation circuitry, including high voltage capacitors that are charged and discharged to deliver cardioversion/defibrillation shocks, and a low voltage battery employed for powering the circuitry and delivering pacing pulses.

In one embodiment, housing 30 includes a first electrode 60 formed on a major surface of housing 30. In one embodiment, first electrode 60 is sized between about 100 mm$^2$ and 1,000 mm$^2$, for example, and is formed of a solid conductive sheet or a conductive mesh formed of a biocompatible electrode material, e.g., titanium, nickel alloys, stainless steel alloys, platinum, platinum iridium alloy, and mixtures thereof. When positioned, tissue adhesive may be employed to secure housing 30 at the desired subcutaneous site and prevent migration. Alternatively, the site is exposed through a minimally invasive surgical procedure and housing 30 is sutured at the site to prevent device migration. The resulting cosmetic appearance can be improved by forming the housing 30 to be as thin as possible, minimizing the bulk of header 32 and curving the major housing surfaces to conform well to the curvature of the thorax at the recommended posterior and anterior or other implantation sites.

In one embodiment, header 32 is configured for permanent connection to proximal end 36 of lead 34. In one embodiment, header 32 is configured for removable connection with proximal end 36 of lead 34.

Figure 2:
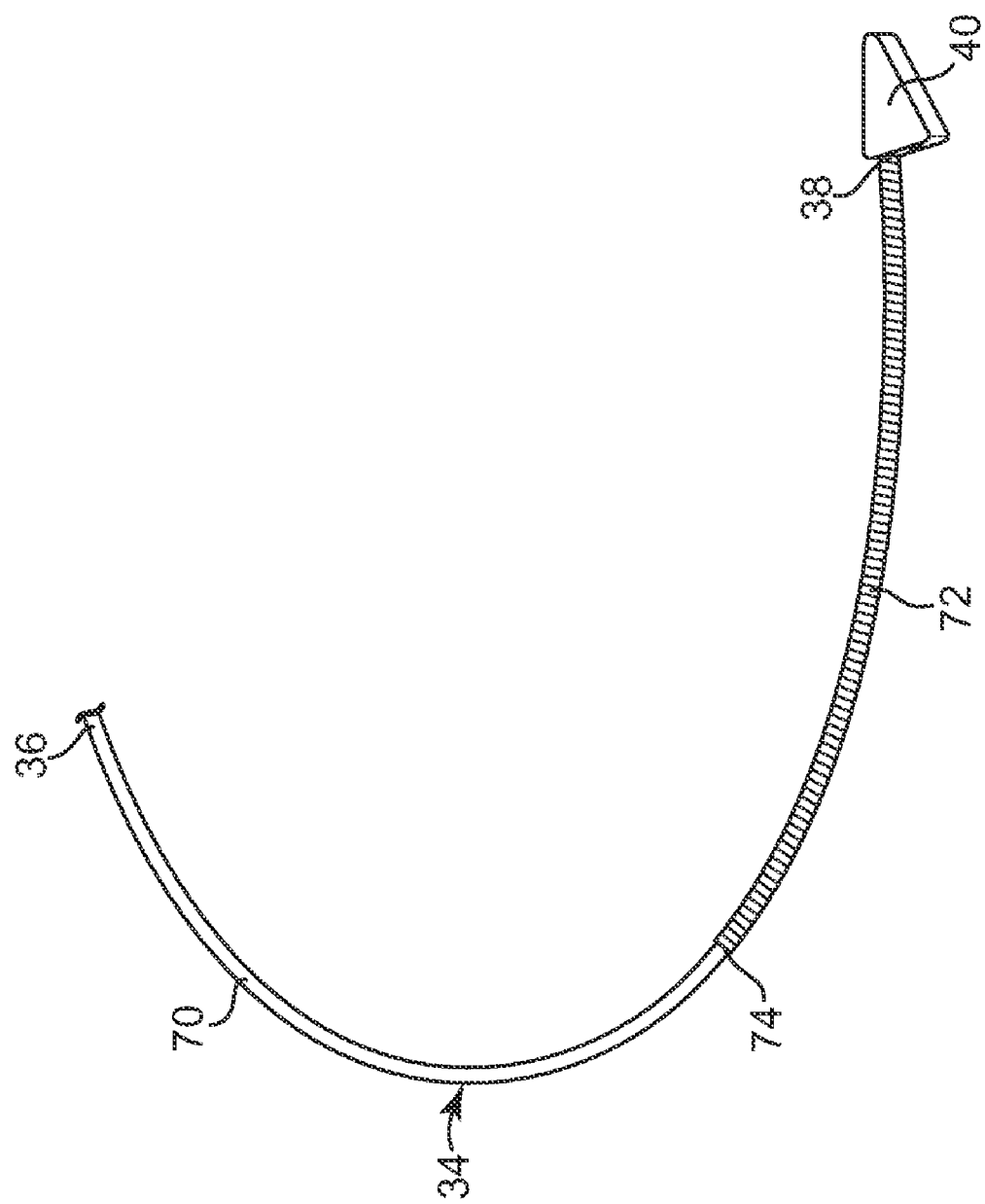
FIG. 2 is a perspective view of the subcutaneous implantable lead and the lead tip as illustrated in FIG. 1.

FIG. 2 is a perspective view of lead 34. In one embodiment, lead 34 includes a body 70 extending between proximal end 36 and distal end 38, and a second electrode 72 that extends a portion of the length of body 70, for example between distal end 38 and electrode end 74. Body 70 of lead 34 generally includes at least one axially disposed conductive wire (not shown) extending from proximal end 36 to lead tip 40, where the wire is electrically insulated in a suitable manner. In one embodiment, second electrode 72 is provided as a coil and is referred to herein as a defibrillation coil 72 or defibrillation electrode 72.

It is desirable to provide a length of lead 34 that is too short to wrap around the patient's thorax. If lead 34 is provided in a length that is too long, lead tip 40 and defibrillation coil 72 could potentially wrap around the patient's thorax to a pectoral position adjacent to housing 30 (FIG. 1) and undesirably diminish the efficiency of shocks delivered by ICD 20. In one embodiment, lead 34 has a length of approximately 60 cm between proximal end 36 and distal end 38, although lead-lengths of approximately 40-80 cm are also acceptable. In one embodiment, defibrillation coil 72 has a length extending between distal end 38 and electrode end 74 of between approximately 10-30 cm, and preferably the length of defibrillation coil 72 is between approximately 15-20 cm. Other suitable lengths for lead 34 and coil 72 are also acceptable.

In one embodiment, the axially disposed conductive wire within lead 34 is electrically coupled to defibrillation coil 72 at distal end 38 and electrode end 74. Other suitable configurations for the electrically conductive portions of lead 34 are also acceptable.

Figure 3:
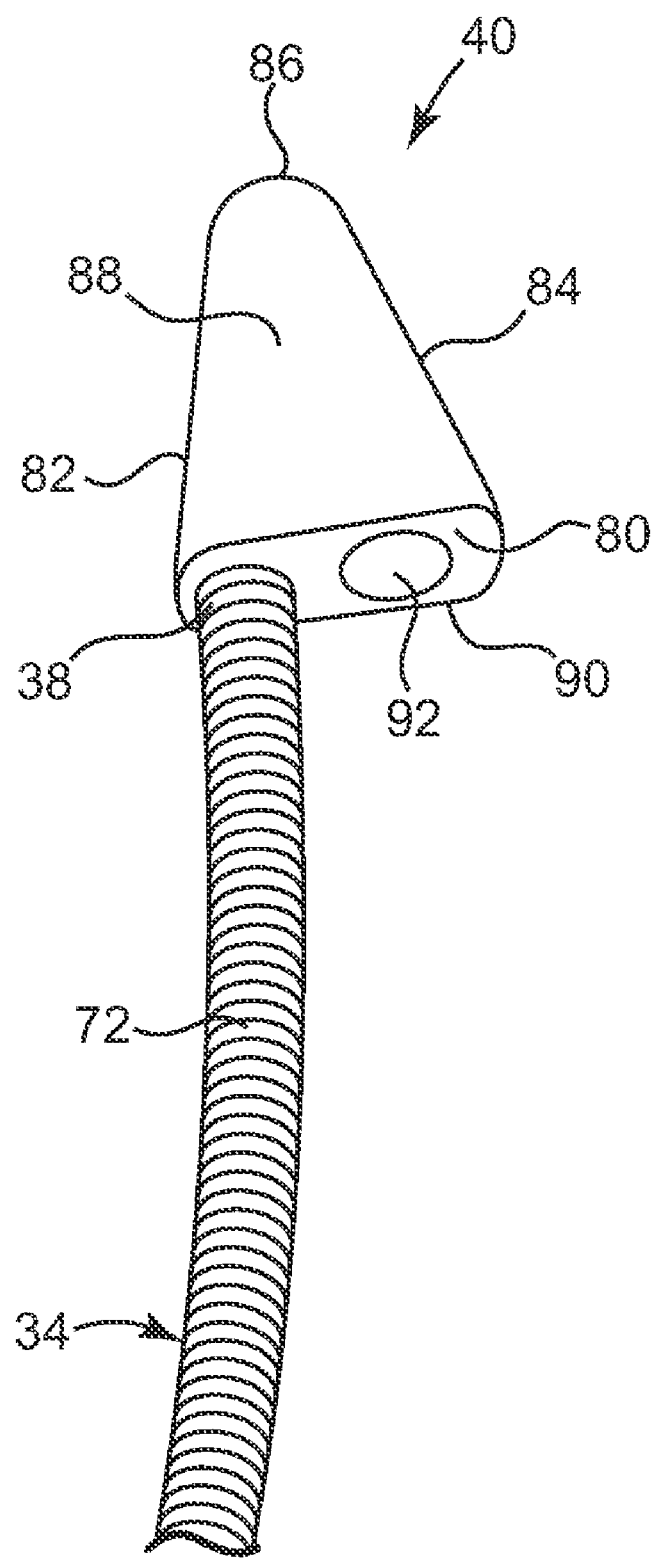
FIG. 3 is a perspective view of the lead tip illustrated in FIG. 2 according to one embodiment.

FIG. 3 is a perspective view of lead tip 40 coupled to lead 34. In one embodiment, lead tip 40 includes a trailing end 80 coupled to lead 34, and a first side 82 and a second side 84 that are non-parallel and extend form trailing end 80 to converge at a leading end 86.

In one embodiment, lead tip 40 includes a first major surface 88 opposite a second major surface 90 and includes a periphery defined by leading end 80 and first and second sides 82, 84. In one embodiment, the periphery of lead tip 40 is arrow-shaped or substantially triangular in shape as illustrated.

In one embodiment, trailing end 80 defines a surface area extending between first and second major surfaces 88, 90, and leading end 86 defines an apex that has a surface area that is less than the surface area of trailing end 80. In this manner, the apex of leading end 86 is configured to wedge between tissue layers without cutting through the skin or thorax as lead tip 40 is advanced subcutaneously. In one embodiment, the triangular or arrow-shaped lead tip 40 is formed to remove all sharp edges and includes radiused edges around the periphery.

In one embodiment, trailing end 80 defines an engagement site 92 or recess 92 that is configured to receive a distal end of a subcutaneous tunneling tool. As described in greater detail below, the tunneling tool is inserted into engagement site 92 and is employed to advance lead tip 40 through subcutaneous tissue. The triangular arrow-shape or wedge-shape of lead tip 40 assists the tunneling tool in placement of lead 34 without the additional use of a sheath or other components.

Suitable materials for forming lead tip 40 include dielectric materials and conductive materials. In one embodiment, lead tip 40 is fabricated from plastic and permanently attached to distal end 38 of lead 34. In one embodiment, lead tip 40 is formed of a dielectric material and includes a conductive coating (e.g., a metal plating) applied to at least one surface. In one embodiment, lead tip 40 is formed of an electrically conducting material, such as metal, and distal end 38 of lead 34 is permanently attached to trailing end 80.

Figure 4A:
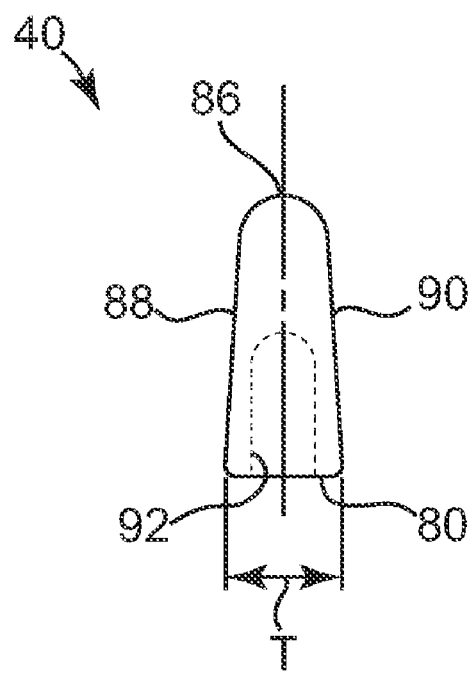
FIG. 4A is a cross-sectional view of the lead tip illustrated in FIG. 3 according to one embodiment.

FIG. 4A is a side view of lead tip 40. In one embodiment, lead tip 40 has a thickness T of approximately 4-6 mm extending between first and second major surfaces 88, 90. The thickness T of trailing end 80 is thicker than the thickness of leading end 86 such that leading end 86 (or apex 86) has a smaller forward area than trailing end 80. In one embodiment, first major surface 88 is not parallel with second major surface 90, such that the major surfaces 88, 90 taper from the thicker trailing end 80 down to the smaller frontal area of leading end 86.

Figure 4B:
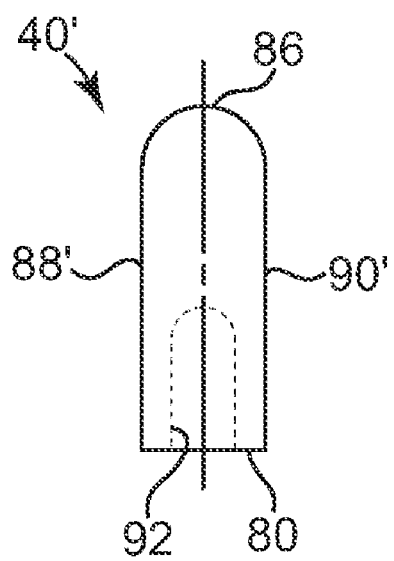
FIG. 4B is a cross-sectional view of another lead tip according to one embodiment.

FIG. 4B is a side view of another lead tip 40' according to one embodiment. Lead tip 40' includes first and second major surfaces 88', 90' that are parallel and extend between trailing end 80 and leading end 86. Parallel major surfaces 88', 90' are associated with a slight increase in tunneling force, which can be desirable. For example, it is desirable to achieve a balance between reducing the tunneling force employed to advance lead tip 40 or 40' subcutaneously through tissue with the possibility of inadvertently puncturing the skin or the thorax if the lead tip is too pointed. To this end, lead tip 40 (FIG. 4A) is fabricated to include a suitable taper of major surfaces 88, 90, and lead tip 40' (FIG. 4B) is fabricated to provide no taper of major surfaces 88', 90'.

Other suitable shapes for lead tip 40 are also acceptable. For example, in one embodiment one or both of major surfaces 88, 90 include a curvature, such as a spherical curvature, that configures a spade-shaped blunt ended lead tip 40 to slide through the subcutaneous tissue.

Figure 5:
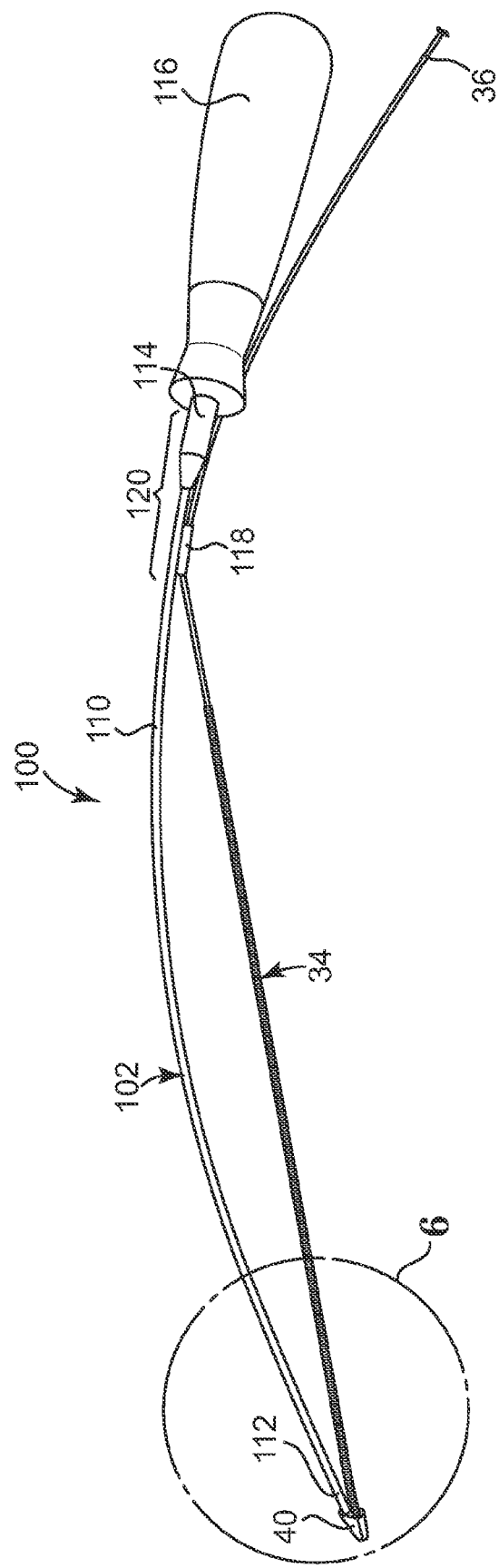
FIG. 5 is a perspective view of a subcutaneous implantable lead system including a lead terminating in a lead tip and a tunneling tool removably attached to the lead tip according to one embodiment.
Figure 6:
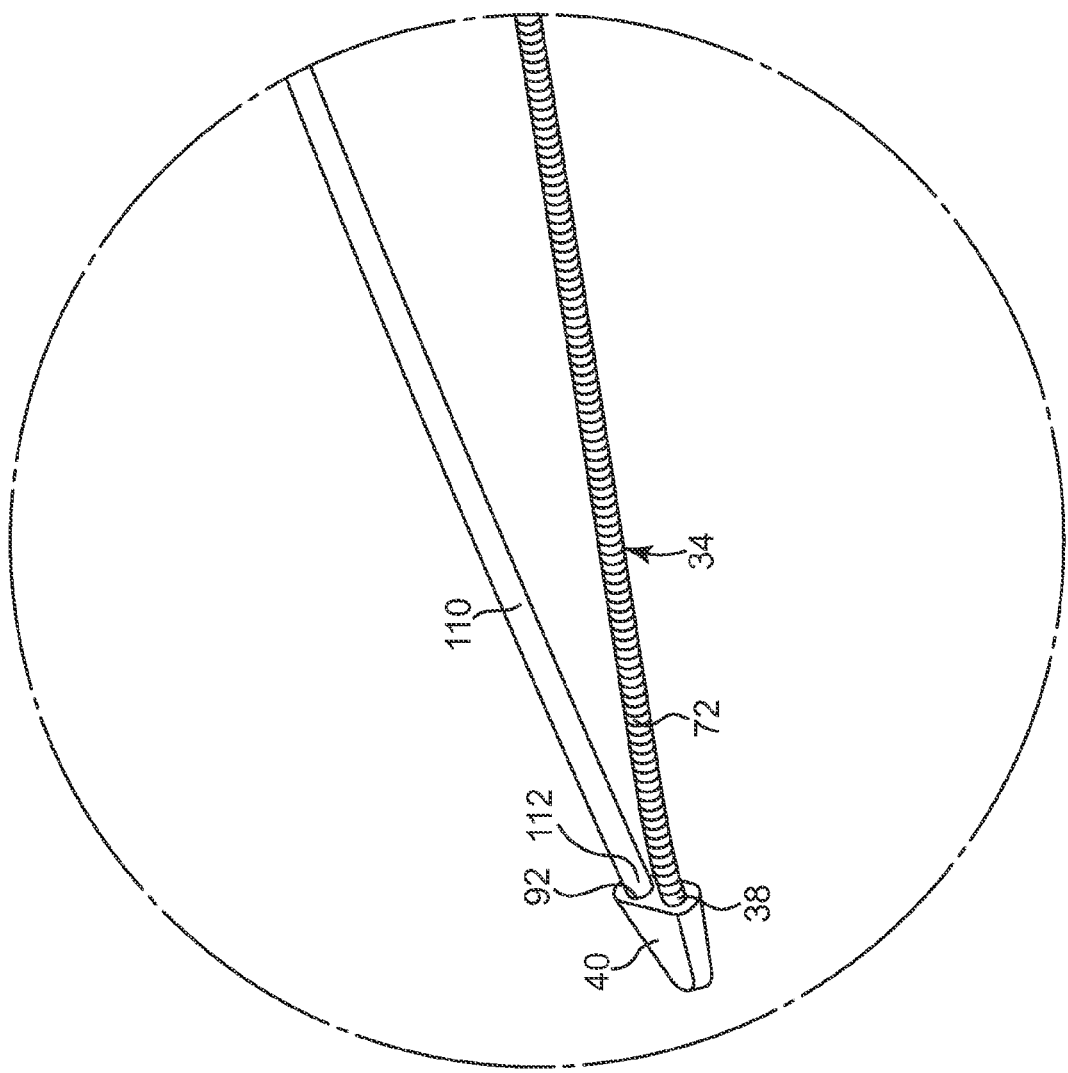
FIG. 6 is a perspective view of a distal portion of the lead system illustrated in FIG. 5.

FIG. 5 is a perspective view of a subcutaneous implantable lead system 100 and FIG. 6 is an enlarged perspective view of the distal end of the system 100 according to one embodiment. Subcutaneous implantable lead system 100 (system 100) includes lead tip 40 coupled to distal end 38 of lead 34 and a tunneling tool 102 that is removably inserted into lead tip 40.

In one embodiment, tunneling tool 102 includes a tool body 110 extending between a distal end 112 that is inserted into engagement site 92 of lead tip 40 and a proximal end 114 that is coupled to a handle 116, and a lead tensioning device 118 attached to a proximal end portion 120 of tool body 110.

In one embodiment, distal end 112 of tunneling tool 102 is sized to be inserted into engagement site 92 (recess 92) to enable tunneling tool 102 to be withdrawn or removed from lead tip 40 after subcutaneous placement of lead 34. It is desirable to maintain control of lead tip 40 when subcutaneously advancing lead tip 40 with tunneling tool 102. To this end, lead tensioning device 118 is configured to clamp or engage a proximal end portion of lead 34 and tension lead 34 taut between lead tip 40 and tensioning device 118. In this manner, lead tip 40 is firmly pulled into engagement with distal end 112 of tunneling tool 102 to enable forward and backward motion of lead tip 40 during placement of lead 34 without inadvertently disengaging tunneling tool 102 from lead tip 40.

In one embodiment, distal end 112 of tunneling tool 102 is configured to slide into and out of engagement with recess 92. In another embodiment, distal end 112 includes threads that are configured to be screwed in a threaded recess 92 to positively engage tunneling tool 102 with lead tip 40. After subcutaneously placing lead 34, tunneling tool 102 is removed by unscrewing distal end 112 from lead tip 40.

With additional reference to FIG. 1, housing 30 provides a first electrode 60 and defibrillation coil 72 provides a second electrode extending at least a portion of the distance along lead 34. It is desirable to maximize the conductive surface area of the electrodes 60, 72 to maximize the efficiency of the electrical shock delivered across the heart H. As noted above, the length of lead 34 is selectively sized to ensure that lead tip 40 does not undesirably wrap from the back of the patient around to the front of the patient, which places a limit on the available electrically conductive surface area. Embodiments described below maximize the electrically conductive surface area of the electrodes of ICD 20 and provide other removable tunneling tools.

Figure 7A:
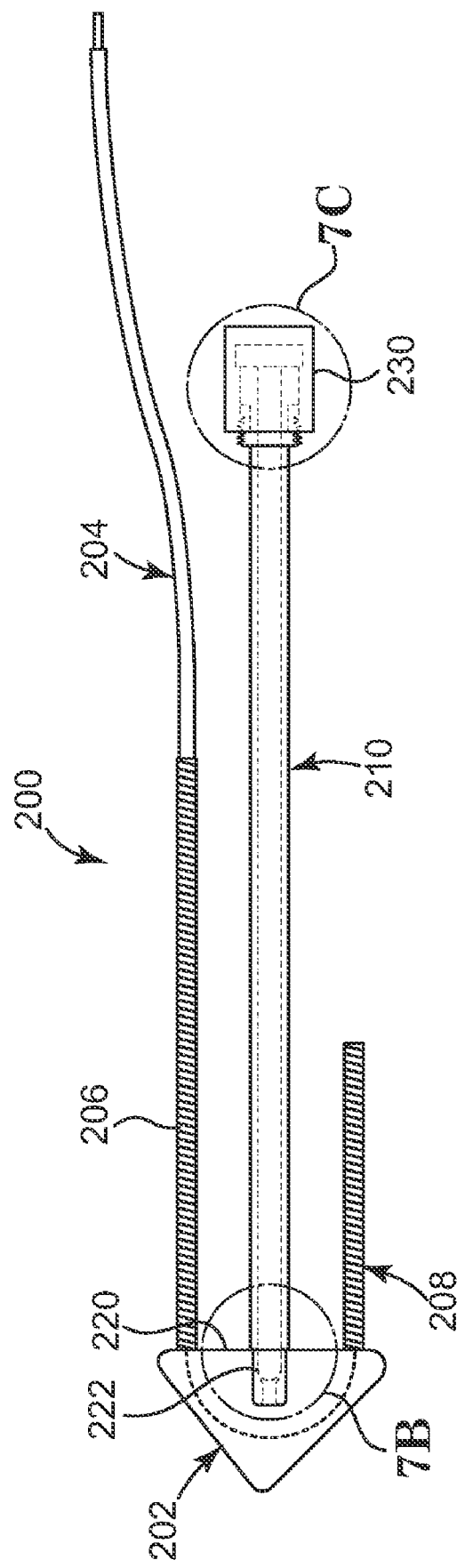
FIG. 7A is a top view of another subcutaneous implantable lead system including a lead terminating in a lead tip and a tunneling tool removably attached to the lead tip according to one embodiment.

FIG. 7A is a top view of another subcutaneous implantable lead system 200 according to one embodiment. Subcutaneous implantable lead system 200 (system 200) includes a lead tip 202, a lead 204 including a primary defibrillation coil 206, one or more satellite defibrillation coils 208, and a tunneling tool 210 configured to removably couple with lead tip 202. Lead tip 202 is similar to lead tip 40 described above but includes one or more satellite defibrillation coils 208 that combine with primary defibrillation coil 206 to provide increased electrically conductive surface area.

In one embodiment, satellite defibrillation coil 208 includes a central conducting wire (insulated within coil 208 and not visible) that electrically connects with a wire of lead 204 at a Y-junction within lead tip 202. In one embodiment, satellite coil 208 has a length between approximately 10-20 cm, although other lengths for satellite coil 208 are also acceptable.

In one embodiment, lead 204 is attached to one side of a trailing end 220 of lead tip 202 and satellite defibrillation coil 208 is attached to another side of trailing end 220. Tunneling tool 210 extends between a distal tip 222 and a handle 230, where distal tip 222 is attachable to trailing end 220 of lead tip 202 between lead 204 and satellite defibrillation coil 208. Handle 230 defines a proximal end of tool 210.

Figure 7B:
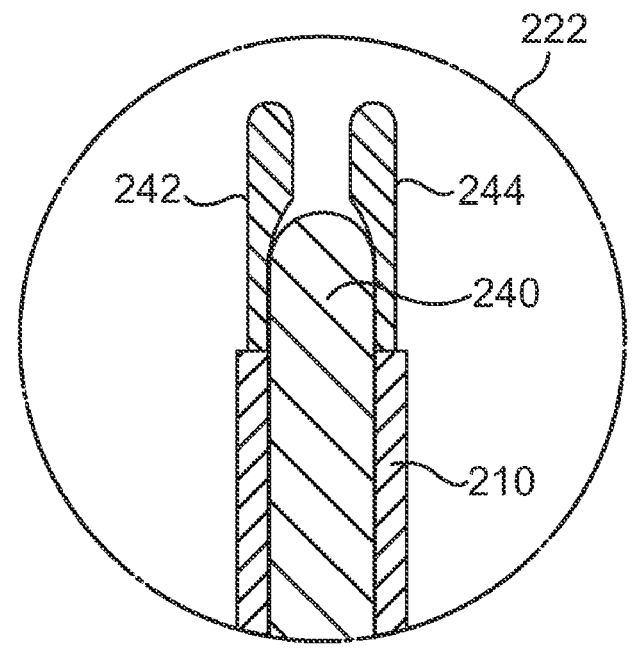
FIG. 7B is a cross-sectional view of a distal portion of the tunneling tool illustrated in FIG. 7A.
Figure 7C:
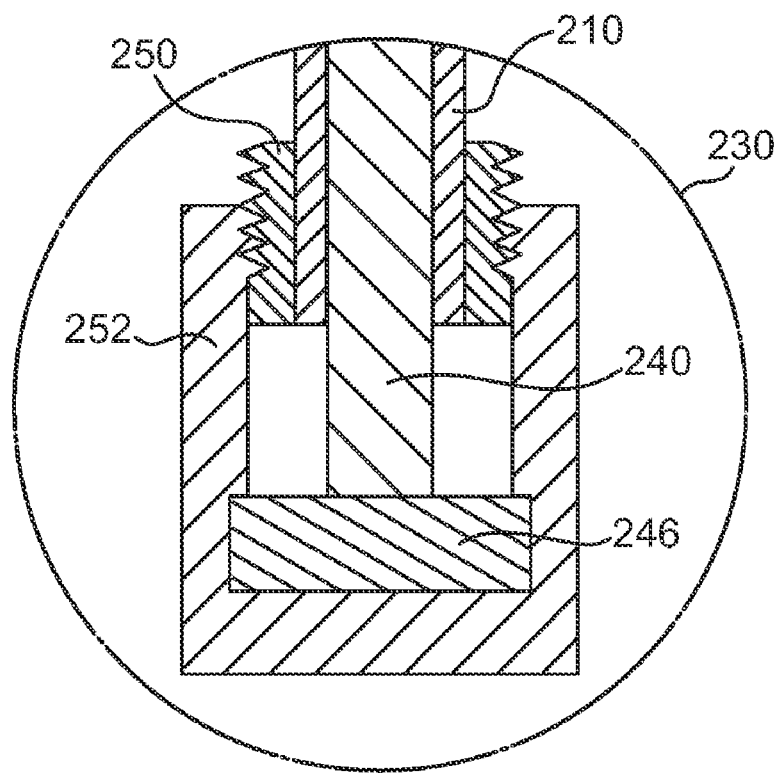
FIG. 7C is a cross-sectional view of a proximal handle portion of the tunneling tool illustrated in FIG. 7A.

FIG. 7B is a cross-sectional view of distal tip 222 and FIG. 7C is a cross-sectional view of handle 230 of tunneling tool 210. Distal tip 222 is configured to positively engage with lead tip 202 (FIG. 7A) and handle 230 is configured to selectively disengage distal tip 222 from lead tip 202.

In one embodiment, a distal tip 222 includes an axially movable pin 240 that is configured to laterally displace prongs 242, 244. In one embodiment, pin 240 communicates with handle 230 such that distal tip 222 is distally activated by manipulating handle 230 at the proximal end of tool 210. FIG. 7B illustrates pin 240 in a retracted state that is configured for engagement with lead tip 202. Moving pin 240 axially forward relative to prongs 242, 244 splays prongs 242, 244 apart and frictionally engages prongs 242, 244 within a recess of lead tip 202. Pin 240 is moved axially by either translational motion or by rotational movement of pin 240.

Pin 240 includes a cap 246 on its proximal end. Handle 230 includes a collar 250 coupled to tool 210 and a grip 252 engaged with cap 246 and collar 250. In one embodiment, grip 252 is engaged with threads of collar 250 such that turning grip 252 clockwise moves grip 252 and pin 240 axially toward lead tip 202, which splays prongs 242, 244 apart to positively engage distal tip 222 with lead tip 202. Conversely, turning grip 252 counter-clockwise moves grip 252 and pin 240 axially in a proximal direction, which retracts pin proximally to enable prongs 242, 244 to disengage from lead tip 202.

Exemplary dimensions for tool 210 include a length of approximately 335 mm, a length of pin 240 (including cap 246) of approximately 330 mm, a width of grip 252 of approximately 25 mm, and prongs 242, 244 being configured to extend by approximately 3 mm when pin 240 is retracted.

Other mechanisms for positively engaging tool 210 to lead tip 202 are also acceptable. For example, in another embodiment tool 210 is provided with an axially located spring-loaded plunger terminating in a pinned connector that couples with lead tip 202, where the pinned connector is activated by a plunger button located on handle 230. Pushing the plunger button selectively ejects the connector pins to disengage tunneling tool 210 from lead tip 202.

Figure 8:
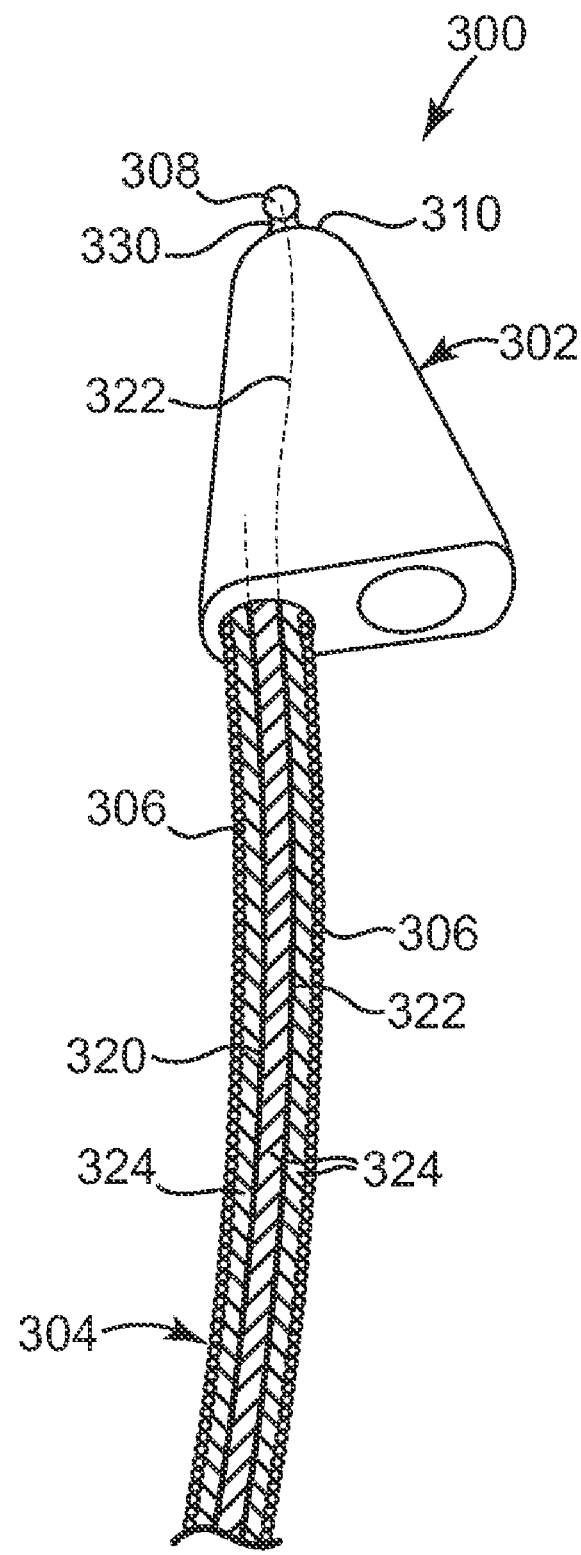
FIG. 8 is a schematic sectional view of another subcutaneous implantable lead according to one embodiment.

FIG. 8 is a schematic sectional view of a subcutaneous implantable lead 300 according to one embodiment. Subcutaneous implantable lead 300 includes a lead tip 302, a lead 304 terminated to lead tip 302 and including a defibrillation electrode 306, and a separate third electrode 308 extending from apex 310 of lead tip 302. In one embodiment, the size and shape of lead tip 302 is similar to the size and shape of lead tip 40 described above. With additional reference to FIG. 1, housing 30 provides a first electrode 60, lead 304 provides a second electrode 306, and third electrode 308 is electrically isolated from first and second electrodes 60, 306 and configured to sense electrogram signals.

In one embodiment, lead 304 includes a first conductive wire 320 extending the length of lead 304 and terminating at lead tip 302, and a second conductive wire 322 extending the length of lead 304 and terminating with third electrode 308. In one embodiment, first wire 320 is electrically insulated from second wire 322 by insulating material 324. In one embodiment, wire 320 is disposed side-by-side with wire 322 and electrically separated by insulation 324. In another embodiment, second wire 322 is coaxial relative to first wire 320 and is insulated with a suitable coaxial insulator.

In one embodiment, third electrode 308 includes a collar 330 that electrically isolates third electrode 308 from lead tip 302. With reference to FIG. 1, when lead 300 is subcutaneously implanted into the patient 22, first electrode 60 provided by housing 30 and second electrode 306 provided by lead 304 combine to provide therapeutic electrical shock to the heart H, and third electrode 308 is electrically isolated from electrodes 60, 306 and configured to sense electrogram signals.

Figure 9:
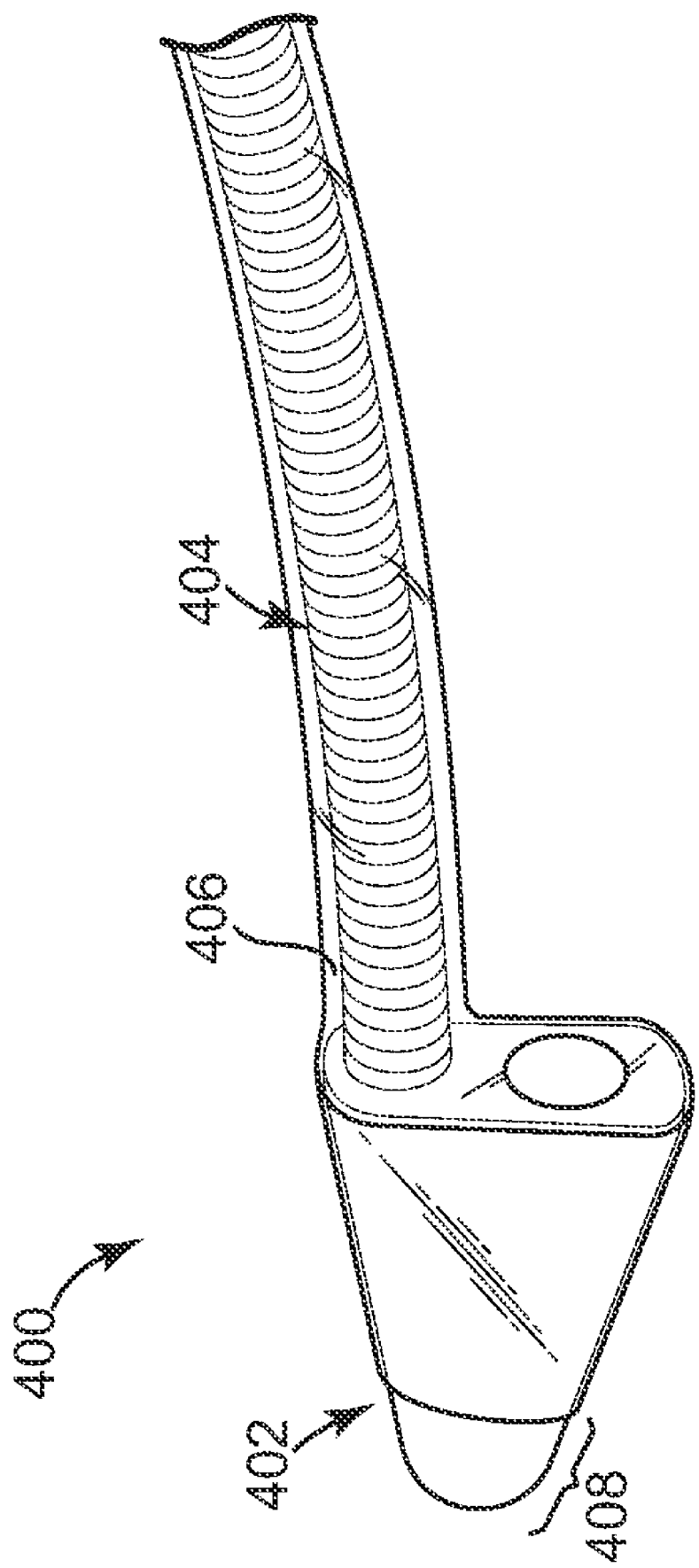
FIG. 9 is a perspective view of a subcutaneous implantable lead attached to a lead tip and coated so only a distal apex of the lead tip is electrically conductive.

FIG. 9 is a perspective view of a subcutaneous implantable lead 400 according to one embodiment. Subcutaneous implantable lead 400 includes a lead tip 402, a lead 404 terminated to lead tip 402, and an electrically non-conductive coating 406 applied over lead 404 and a portion of lead tip 402 so only a distal apex 408 of lead tip 402 is electrically conductive. Lead tip 402 is similar in conformation to lead tip 40 described above, except only distal apex 408 is electrically conducting. Lead 404 and the trailing end portion of lead tip 402 are covered by electrically non-conductive coating 406, such that electrically conducting distal apex 408 is exposed and configured for electrocardiogram measurement.

What is claimed is:

1. A subcutaneous implantable device comprising:
   a lead having a proximal end and a distal end;
   a defibrillation electrode disposed along a portion of the lead between the proximal end of the lead and the distal end of the lead; and
   a lead tip located distally relative to the distal end of the lead, the lead tip comprising:
      a trailing end coupled to the distal end of the lead,
      a first major surface opposite a second major surface, and
      first and second non-parallel sides extending from the trailing end, the first and second non-parallel sides converging to a leading end that is located distally relative to the trailing end and configured to wedge between tissue layers as the lead is advanced subcutaneously, wherein the trailing end, first and second non-parallel sides, and leading end define the peripheries of the first and second major surfaces.

2. The subcutaneous implantable device of claim 1, wherein the trailing end of the lead tip comprises at least one engagement site that is configured to receive a distal end of a subcutaneous implant tool.

3. The subcutaneous implantable device of claim 1, wherein at least a portion of the surface of the lead tip is electrically conductive and configured to sense electrogram signals.

4. The subcutaneous implantable device of claim 3, wherein a portion of the lead tip proximate to the distal end of the lead is covered with an electrically non-conductive material such that only a distal apex portion of the lead tip is electrically conductive.

5. The subcutaneous implantable device of claim 1, wherein the first and second non-parallel sides of the lead tip extend between opposing parallel major surfaces of the lead tip.

6. The subcutaneous implantable device of claim 1, wherein the lead tip comprises a substantially triangular periphery defined by the first and second non-parallel sides and the trailing end.

7. The subcutaneous implantable device of claim 1, wherein the leading end of the lead tip comprises an apex of the substantially triangular periphery, the apex having a surface area that is less than a surface area of the trailing end.

8. The subcutaneous implantable device of claim 1, further comprising:
   at least one satellite electrode coupled to the trailing end of the lead tip, the at least one satellite electrode electrically coupled with the defibrillation electrode at the lead tip.

9. The subcutaneous implantable device of claim 1, further comprising:
   a leading electrode disposed on a leading end of the lead tip, the leading electrode electrically isolated from the defibrillation electrode and configured to sense electrogram signals.

10. The subcutaneous implantable device of claim 1, further comprising:
    an implantable cardiodefibrillator (ICD) coupled to the proximal end of the lead.

11. A subcutaneous implantable lead system comprising:
    a lead having a proximal end and a distal end, the lead comprising a defibrillation electrode disposed between the proximal end of the lead and the distal end of the lead;
    a lead tip located distally relative to the distal end of the lead and coupled to the distal end of the lead, the lead tip comprising opposed major surfaces each having a substantially triangular periphery defined by a trailing side and first and second non-parallel sides extending from the trailing side that converge to a leading apex of the lead tip, wherein the trailing side is coupled to a distal end of the defibrillation electrode and comprises a tool engagement site, and wherein the leading apex is located distally relative to the trailing side; and
    a tunneling tool configured to removably couple with the tool engagement site and subcutaneously advance the lead tip and the lead.

12. The lead system of claim 11, wherein the tool engagement site comprises a recess formed in the trailing side of the lead tip, and a distal end of the tunneling tool is insertable into the recess for subcutaneously advancing the lead tip and removable from the recess for removal of the tunneling tool.

13. The lead system of claim 11, wherein the tunneling tool comprises a lead tensioning device that is configured to maintain tension on the lead between the lead tip and a proximal end portion of the tunneling tool.

14. The lead system of claim 11, wherein the lead tensioning device comprises a lead clamp coupled to a proximal end portion of the tunneling tool.

* * * * *